US011454626B2

(12) United States Patent
Alexandrov et al.

(10) Patent No.: US 11,454,626 B2
(45) Date of Patent: Sep. 27, 2022

(54) SINGLE-CELL IMAGING MASS SPECTROMETRY

(71) Applicant: EUROPEAN MOLECULAR BIOLOGY LABORATORY, Heidelberg (DE)

(72) Inventors: Theodore Alexandrov, Heidelberg (DE); Luca Rappez, Heidelberg (DE)

(73) Assignee: EUROPEAN MOLECULAR BIOLOGY LABORATORY, Heidelberg (DE)

(*) Notice: Subject to any disclaimer, the term of this patent is extended or adjusted under 35 U.S.C. 154(b) by 429 days.

(21) Appl. No.: 16/603,701

(22) PCT Filed: Apr. 13, 2018

(86) PCT No.: PCT/EP2018/059515
§ 371 (c)(1),
(2) Date: Oct. 8, 2019

(87) PCT Pub. No.: WO2018/189365
PCT Pub. Date: Oct. 18, 2018

(65) Prior Publication Data
US 2020/0057049 A1 Feb. 20, 2020

(30) Foreign Application Priority Data
Apr. 13, 2017 (EP) .................................... 17166487

(51) Int. Cl.
| G01N 33/50 | (2006.01) |
| C12N 5/00 | (2006.01) |
| H01J 49/00 | (2006.01) |
| H01J 49/16 | (2006.01) |
| G01N 33/552 | (2006.01) |
| G01N 33/483 | (2006.01) |
| G01N 33/487 | (2006.01) |

(52) U.S. Cl.
CPC ....... *G01N 33/5005* (2013.01); *C12N 5/0068* (2013.01); *G01N 33/4833* (2013.01);
(Continued)

(58) Field of Classification Search
CPC .......... G01N 33/5005; G01N 33/6848; G01N 33/4833; G01N 33/48728; G01N 33/552;
(Continued)

(56) References Cited

U.S. PATENT DOCUMENTS 6,287,765 B1 * 9/2001 Cubicciotti ............ C07H 21/00
536/23.1
7,297,518 B2 * 11/2007 Quake .................. C12Q 1/6874
435/6.12
(Continued)

FOREIGN PATENT DOCUMENTS

| CN | 106153538 A | 11/2016 |
| WO | 2015128490 A1 | 9/2015 |
| WO | 2016090356 A1 | 6/2016 |

OTHER PUBLICATIONS

Zavalin et al. "Direct imaging of single cells and tissue at subcellular spatial resolution using transmission geometry MALDI MS." Journal of Mass Spectrometry 47(11): 1473-1481 (2012).
(Continued)

*Primary Examiner* — Kiet T Nguyen
(74) *Attorney, Agent, or Firm* — Nixon Peabody LLP; Mark J. Fitzgerald; Nicole D. Kling

(57) ABSTRACT

The present invention relates to a method for single-cell imaging mass spectrometry (MS) by correlating an optical image of a cell sample with an MS image. The method of the invention is in particular useful in research to test concomitantly optical and molecular phenotypes at a single-cell resolution.

20 Claims, 8 Drawing Sheets

Figure 1:
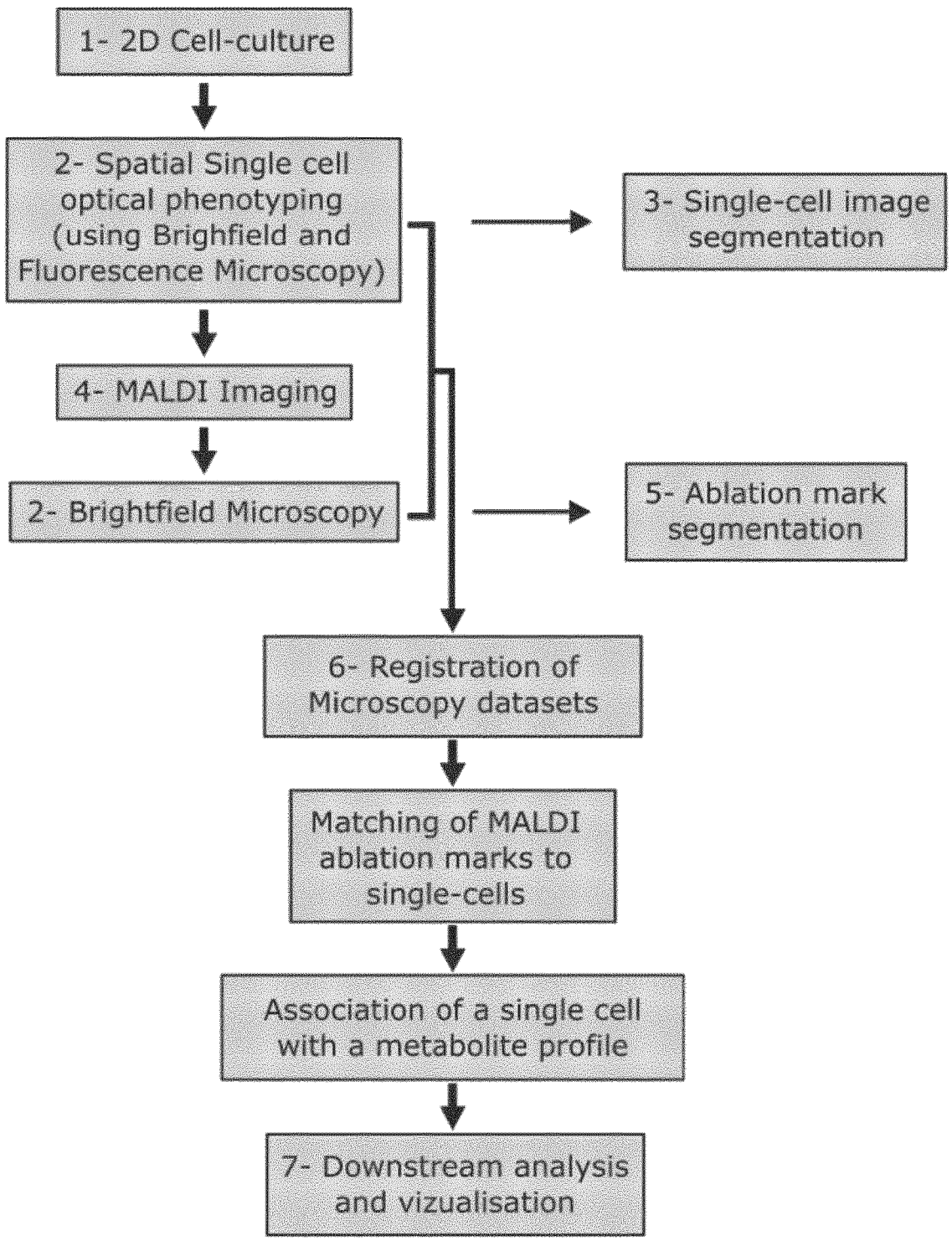

(52) U.S. Cl.
CPC ..... *G01N 33/48728* (2013.01); *G01N 33/552* (2013.01); *H01J 49/0004* (2013.01); *H01J 49/0031* (2013.01); *H01J 49/164* (2013.01)

(58) Field of Classification Search
CPC .. H01J 49/0004; H01J 49/0031; H01J 49/164; C12N 5/0068
USPC ........................................................ 250/282
See application file for complete search history.

(56) References Cited

U.S. PATENT DOCUMENTS

| | | | |
|---|---|---|---|
| 7,981,604 B2* | 7/2011 | Quake | C12Q 1/6869 435/6.12 |
| 2015/0364307 A1 | 12/2015 | Agar et al. | |

OTHER PUBLICATIONS

Buckle et al. "Hybrid Imaging Labels: Providing the Link Between Mass Spectrometry-Based Molecular Pathology and Theranostics." Theranostics 7(3): 624-633 (2017).

Ferreira et al. "Fiducial Markers for Distribution of Drug and Excipient on Tablet Surfaces by Multimodal Desorption Electrospray Ionization—Mass Spectrometry (DESI-MS) Imaging." Analytical Letters 47(1): 91-101 (2014).

Liu et al. "Mass spectrometry imaging of small molecules using desorption/ionization on silicon." Analytical chemistry 79(10): 3535-3541 (2007).

Ostrowski et al. "Secondary ion MS imaging to relatively quantify cholesterol in the membranes of individual cells from differentially treated populations," Analytical chemistry 79(10): 3554-3560 (2007).

* cited by examiner

SINGLE-CELL IMAGING MASS SPECTROMETRY

CROSS REFERENCE TO RELATED APPLICATIONS

This application is a 35 U.S.C. § 371 National Phase Entry Application of International Application No. PCT/EP2018/059515 filed Apr. 13, 2018, which designates the United States, and which claims benefit under 35 U.S.C. § 119(a) of European Application No. 17166487.3 filed Apr. 13, 2017, the contents of each of which are incorporated herein by reference in their entireties.

The present invention relates to method for single-cell imaging mass spectrometry (MS) by correlating an optical image of a cell sample with an MS image. The method of the invention is in particular useful in research to test concomitantly optical and molecular phenotypes at a single cell resolution.

BACKGROUND OF THE INVENTION

Every cell is unique. Metabolites define the composition of each cell and play key roles in essential intracellular processes of energy production and uptake, signaling, regulation, and cell death. In the last few years, a remarkable progress of single-cell technologies has revealed profound heterogeneity of cells at the morphological, genomic, epigenomic, transcriptomic, and proteomic levels. Obtaining metabolite signatures of individual cells and linking them to cellular phenotypes is of paramount importance for a holistic understanding of these processes. This requires high-throughput single-cell metabolomics that is not generally attainable due to the limited sensitivity, low throughput, and disruptiveness of conventional metabolomics methods.

Imaging mass spectrometry (imaging MS) is a technique used to determine (and visualize) the spatial distribution of endogenous and exogenous small molecules and lipids in a sample by acquiring spatially resolved mass spectra. In recent years, imaging MS is increasingly used to analyze the spatial distributions of compounds in tissue sections (Caprioli; U.S. Pat. No. 5,808,300 A), particularly by using matrix assisted laser desorption/ionization (MALDI). However, imaging MS can also be used to analyze other types of samples, like plates of thin layer chromatography (Maier-Posner; U.S. Pat. No. 6,414,306 B1), gels of an electrophoresis or blot membranes. All spatially resolved mass spectra of a sample constitute a mass spectrometric imaging data set $S(x, y, m)$. The mass spectrometric imaging data set $S(x, y, m)$ of a sample can be viewed as a collection of multiple mass images $S(x, y, mk)$ of different masses or mass ranges mk, that is, $S(x, y, m)$ can be divided into mass ranges each generating a mass image.

The Caprioli group has proposed a raster scan method to acquire spatially resolved MALDI mass spectra of tissue sections (Caprioli et al (1997) *Analytical Chemistry*). A tissue section is prepared on a slide or sample plate covered with a matrix layer and then scanned with laser pulses of a focused laser beam in the x- and y-directions, often with several hundred pixels in both directions. In order to raster an entire tissue section, the sample plate is moved by a stage along the x- and y-direction. Every pixel (focus region of the laser beam) on the tissue section is irradiated at least once in the imaging process, and usually ten to a hundred times. The ions generated in the multiple MALDI processes are analyzed in a mass analyzer, either by using a time-of-flight mass spectrometer with axial ion injection or quadrupole time-of-flight mass spectrometer or Fourier Transformation-based mass spectrometer (including FTICR or Orbitrap). The multiple mass spectra acquired at a single pixel are added to a sum spectrum and the sum spectrum is assigned to the pixel.

Feasibility of metabolomics analysis of individual isolated human cells or single-to-a-few microbial or algal cells was recently demonstrated. The Sweedler group established methods for analysis of individual isolated neurons using CE ESI MS from individual isolated cells or from cytoplasm isolated using a patch clamp pipet. The Zenobi group developed a technology for studying cells deposited onto a microarray of hydrophilic reservoirs with a few cells per spot ($1 \leq n \leq 15$) using MALDI MS and applied it to study *S. cerevisiae* and unicellular microalga *C. reinhardtii*. The Vertes group studied small populations ($1 \leq n \leq 80$) of *S. cerevisiae* cells deposited onto silicon nanopost arrays and analyzed the populations using LDI MS. Nemes group has analyzed dissected *Xenopus laevis* oocytes using CE-nanoESI MS. The Masujima group analyzed human hepatocellular carcinoma cells HepG2 by using a micromanipulated nanospray tip targeted by laser microscopy. The Spengler group demonstrated direct imaging of metabolites, lipids and peptides in a single-celled ciliate *P. caudatum* using atmospheric pressure MALDI imaging MS.

Imaging MS, originally developed for protein imaging, is becoming a method of choice for metabolite imaging in tissues and cell cultures. Imaging MS is a prominent avenue for single-cell analysis as demonstrated by recent studies of individual isolated human cells. Till recently, the bottlenecks of using imaging MS for single-cell metabolomics were: lack of spatial single-cell resolution, limited sensitivity and low coverage of metabolite classes, and lack of bioinformatics methods for metabolite identification.

Therefore, it was the underlying problem of this invention to provide a novel approach for single cell metabolomics using imaging MS, in particular MALDI imaging.

The above problem is solved in a first aspect by a method of single cell(s) imaging mass spectrometry (imaging MS), the method comprising the steps of
 (a) Culturing cell(s) on a substrate,
 (b) Phenotyping the cell(s) by microscopy to obtain at least one optical (preferably fluorescent) image showing an optical phenotype of the cell(s),
 (c) Phenotyping of the cell(s) by imaging MS to obtain a MS molecular image showing a molecular phenotype of the cell(s),
 (d) Comparing the optical image and the MS molecular image to compare and/or correlate and/or assign the optical phenotype of at least one single cell with the corresponding molecular phenotype of the at least one single cell,
wherein steps (b) and (c) are performed in any order/sequence, but preferably step (b) is performed before step (c).

In some embodiments step (b) includes obtaining at least one optical (preferably fluorescent) image showing an optical phenotype of the cell(s) that can be used to quantify general phenotypical properties of cell population(s) (e.g. number of cells, viability, motility), morphological properties of individual cells (e.g. area, elongation) as well as spatial properties of the cells (local spatial crowding, number of neighbors).

Preferably the imaging MS of the invention is performed for a single cell or individual cells amongst a plurality of cells in a cell culture. The method of the invention surprisingly allows in a plurality of co-cultured cells to identify subpopulations of cells associated with a particular cell phenotype or subpopulations of cells having the same molecular profile as an individual cell of interest.

The term "imaging MS" shall in context of the invention pertain to any MS analysis method that when applied to a cellular sample will produce visible ablation marks on the sample. Such methods in particular comprise matrix-assisted laser desorption/ionization (MALDI) imaging, Secondary-ion mass spectrometry (SIMS) imaging with either time-of-flight (TOF) or Orbitrap analyzer, infrared-MALD-electrospray ionization (IR-MALDESI) imaging, $MALDI_2$ imaging, Laser ablation electrospray ionization (LAESI) imaging. In preferred embodiments the imaging MS of the invention is MALDI imaging.

The method of the invention is in particular useful for correlating one or more optical phenotypes of one or more cell(s) with a metabolic phenotype. Therefore, in preferred embodiments, the invention is useful to identify one or more subpopulations of one or more cells in the plurality of cells, wherein the subpopulation is characterized by a defined specific molecular profile determined by imaging MS or a combination of a defined molecular profile and quantified properties of cell(s) obtained using microscopy.

The method of the invention in preferred embodiments is a high throughput method.

As used herein, the term "molecular phenotype" refers to any stage or changes that provide information regarding the molecular composition of a cell, preferably its metabolic state, including changes and composition (concentrations) of a cell's metabolites, such as protein changes, nucleic acid changes, carbohydrate changes, lipid changes, etc.

As used herein, the term "optical phenotype" refers to any stage or changes that provide information about a cell's state that can be visualized, for example using a bright field microscope, fluorescent dyes, fluorescent sensors, or any other molecular labels or sensors. Such information in particular includes cell size, morphology, cell position, position of individual cellular components such as cell organelles, proteins, nucleic acids, or any other cellular molecule that can be optically tracked by, for example, a labeled nucleic acid probe or antibody, or molecules.

As used herein, the term "optical image" refers to an image representing one or more bright-field or fluorescent emissions. For example, the fluorescent emissions can be between about 625 nm and about 825 nm. Fluorescent images are typically obtained by applying an absorption wavelength to an object of interest and simultaneously or after a delay, capturing an image of fluorescent emissions. Fluorescent images can be obtained using a variety of devices including fluorescent microscopes, which is preferred. The fluorescent image can, in some embodiments, be a two-dimensional image consisting of a plurality of pixels, each of which can be a numerical representation of the intensity of the bright field or fluorescence as at particular location.

The term "MS molecular image" refers to a two-dimensional representation of the results of a imaging MS analysis in a plurality of pixels each of which associates the molecular (metabolic) results of the analysis to a location.

In the method of the invention it is preferred that the cell(s) are cultured in a monolayer, preferably a monolayer of adherent cells. Any adherent cells can be used for this purpose, as long as such cells can be sufficiently segregated so not significant overlap between single cells occur. Several cell lines were tested with the method of the invention, such as macrophages (RAW 264.7, ATCC® TIB-71™), HeLa cells (ATCC® CCL-2™), intestinal epithelial cells (C2BBe1, ATCC® CRL-2102™), T84, ATCC® CCL-248™), hepatocytes (HepaRG). Although these cell types are preferred, the invention was shown to be broadly applicable and shall not be restricted to any specific type of adherent cell.

In another preferred embodiment the method of the invention in step (d) comprises that the MS molecular image and the optical image are correlated by direct comparison of the images, in particular by overlaying (in high precision) both images, with the MS intensities associated with the ablation marks produced during the imaging MS analysis. An example of an overlay of these images is provided in FIG. 2. Alternatively, the comparison may be performed by mapping the ablation marks onto an optical image by converting the imaging MS coordinates into the pixels of an optical image.

The substrate of the invention may be any material suitable for cell culture and is in particular a translucent substrate, such as a translucent plastic or glass substrate, preferably a glass slide or coverslip. Also cell culture suitable plastic well plates or permeable supports can be used.

The term "microscopy" in context of the invention shall in particular refer to bright-field and/or fluorescent microscopy. For bright-field transmitted light microscopes, light is aimed toward a lens beneath a stage called the condenser, through the sample specimen, through an objective lens, and to the eye through a second magnifying lens, the ocular or eyepiece. The object to be inspected is normally placed on a clear glass slide and light is transmitted through the object, which makes the object appear against a bright background hence the term "bright-field." The objects in the light path are seen because natural pigmentation or stains absorb light differentially, or because they are thick enough to absorb a significant amount of light despite being colorless. Fluorescence microscopy applies a light microscope used to study properties of organic or inorganic substances using fluorescence instead of, or in addition to, reflection and absorption. The fluorescence microscope is based on the phenomenon that certain material emits energy detectable as visible light when irradiated with the light of a specific wavelength. The sample can either be fluorescing in its natural form (like chlorophyll) or it may be treated with a fluorescing stain (fluorescent agents or labelled antibodies).

In another embodiment step (d) comprises assigning location coordinates to each cell in the MS molecular image and the optical image, and thereby assigning the optical phenotype of each cell with its molecular phenotype.

In yet another embodiment, multiple but different optical images are obtained; and step (d) comprises comparing each of the multiple optical images to the MS molecular image to correlate/assign each optical phenotype of the multiple optical images of each cell with its molecular phenotype.

In another embodiment, at least one optical image is an image of a Hoechst staining of the cell(s).

In another embodiment, the substrate comprises fiducial marks for image registration.

In another embodiment, step (d) comprises the identification of each cell in the optical image, for example using a cell segregation algorithm, preferably wherein a Hoechst staining image is used to identify cell nuclei.

In another embodiment, the method of the invention comprises a step (c') subsequent to step (c), wherein step (c') comprises obtaining an optical ablation mark image, for example by bright field microscopy. The optical ablation mark image is useful for assigning location coordinates to the ablation marks and for segregating them (as explained herein elsewhere). The term "ablation mark" in context of the invention shall refer to an area on the sample which was subjected to a laser probing during MS, in particular MALDI analysis. Preferably, the ablation marks in the ablation mark image are segregated, preferably using Fourier transformation.

Hence, the present invention in some preferred embodiments comprises obtaining optical images from two time points, one before subjecting the cells to MS, and one after subjecting the cells to MS (the latter being the ablation mark imaging). However, one cell can be sampled more than once as well as an ablation mark can represent a convoluted metabolic readout from more than one cell or from both intracellular metabolome and extracellular background. Therefore, in some embodiments a normalization strategy to compensate for these effects and to assign normalized metabolite intensities to individual forms part of the present invention. The invention therefore might comprise a step of estimating the molecular intensity of a cell according to the formula presented in FIG. 9, right hand side.

The step of estimating metabolite intensities (normalization step) in some embodiments may comprise the following sub-steps (for each cell):
- selecting the ablation marks which overlap with the cell by over than 10%, preferably 20%, most preferably equal or more than 30% of their ablation area;
- normalizing the metabolite intensities coming from an ablation mark by dividing them by the ratio of the sampling area (defined as the number of pixels of the intersection of the ablation mark and any cell region) to the area of the ablation mark;
- calculating each cells normalized metabolite intensities as the weighted average normalized intensities of the associated ablation marks where the weights are defined as the ratio of the shared pixels.

In some specific embodiments, in order to account for the variations in permeabilization efficiency between the biological replicates, single-cell fluorescence intensities may be normalized by dividing them by the median DAPI (or other cell nuclei staining) intensity (median over a well).

In some embodiments of the invention any one of, or any combination of, or all of, the specifically described steps of the method of the invention in Example 1, or in the Material and Methods section, shall form part of the herein described invention.

In context of the invention it is preferred that the ablation marks are segregated by a method comprising at least the steps of:
(a) 2D fast Fourier transformation (FFT) of the ablation mark image,
(b) Applying a Gaussian filter on the resultant of step (a),
(c) Subtracting the resultant of step (b) from the resultant of step (a),
(d) Thresholding the coefficients of (c) to obtain a binary mask,
(e) Applying a morphological image dilation to the binary mask,
(f) Computing an inverse FFT showing ablation marks to obtain an FFT ablation mark image,
(g) Optionally, applying contrast enhancement and/or background reduction to the FFT ablation mark image,
(h) Binarizing the FFT ablation mark image to obtain a binary ablation mark image,
(i) Computing coordinates of individual ablation marks in the binary ablation mark image by centroid estimation.

A detailed explanation of the procedure is provided herein in the example section, in particular in the Materials and Methods.

In preferred embodiments of the invention optical image is aligned with the optical ablation mark image in order to correlate/assign the optical phenotype of each cell with its molecular phenotype.

Preferably, during step (c) a MS matrix is deposited to the cell(s) and subsequently imaging MS is performed. If MALDI imaging is performed, the MALDI matrix is preferably an opaque MALDI matrix to allow for obtaining the optical ablation mark image. Any MALDI matrix is preferred which allows for obtaining the optical (bright-field or fluorescent) ablation mark image.

For the purpose of the present invention it is preferred that MALDI imaging involves the scanning of at least one area of the substrate comprising the cell(s) with a MALDI suitable laser. The scanning preferably does not produce overlapping ablation marks on the substrate. Therefore it is preferred that the laser-focus size is smaller or comparable to the average size of a cell in the studied cell population and is about 1 μm-30 μm and/or that MALDI imaging involves 10-300 laser shots per pixel depending on the type and energy of the laser used.

The following figures, sequences, and examples merely serve to illustrate the invention and should not be construed to restrict the scope of the invention to the particular embodiments of the invention described in the examples. All references as cited herein are hereby incorporated in their entirety by reference.

FIG. 1: Workflow of the MALDI single-cell imaging method of the invention.

Figure 2:
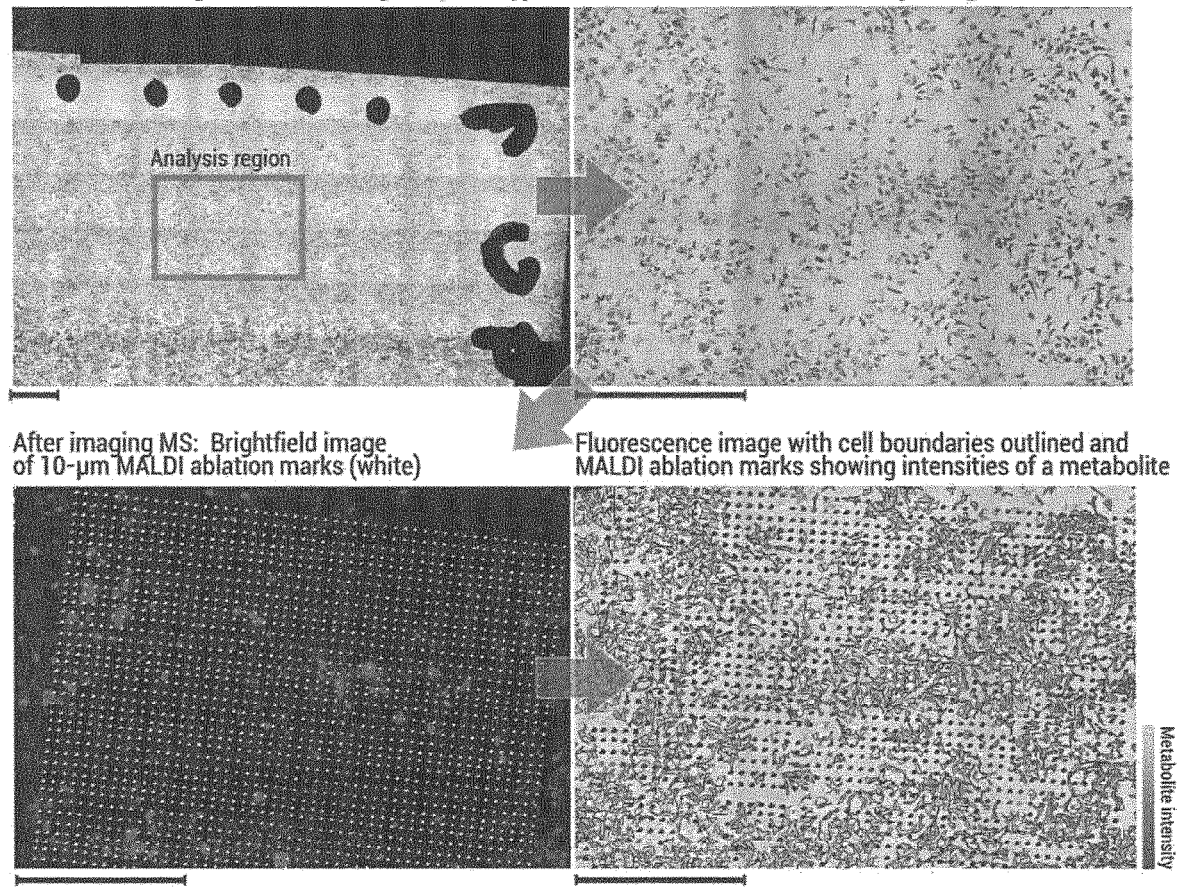

FIG. 2: Illustration of the concept of the high-precision correlative light microscopy-imaging mass spectrometry based on preliminary experiments with adherent cells and AP-SMALDI imaging MS. In the bottom right images, the overlay shows a molecular image with the intensities correlated with the fluorescence phenotype readout. The scale bar corresponds to 1 mm.

Figure 3:
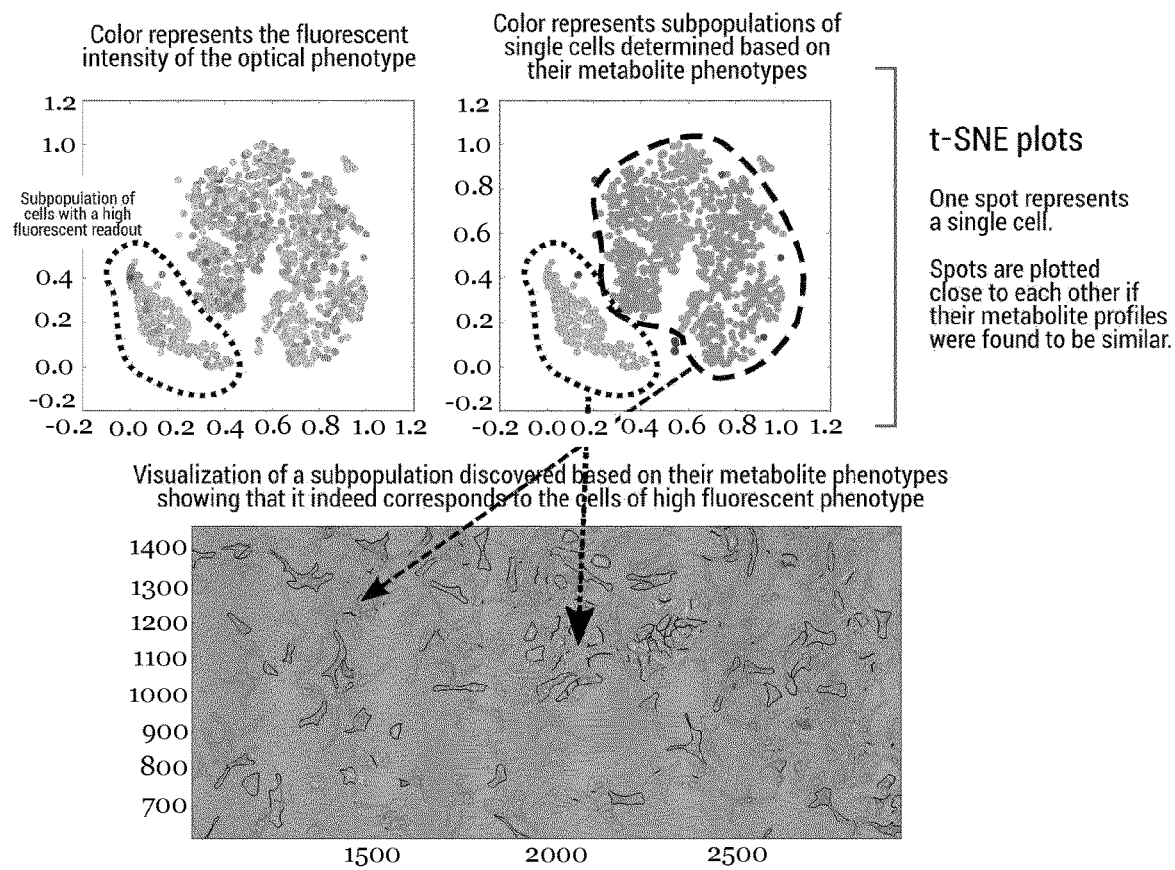

FIG. 3: Demonstration of the method of the invention with a subpopulation of cells which have a specific metabolic phenotype and a specific optical phenotype (high fluorescence); the preliminary experiments with adherent cells and AP-SMALDI imaging MS, with the downstream data analysis using a t-SNE mapping and clustering approach.

Figure 4:
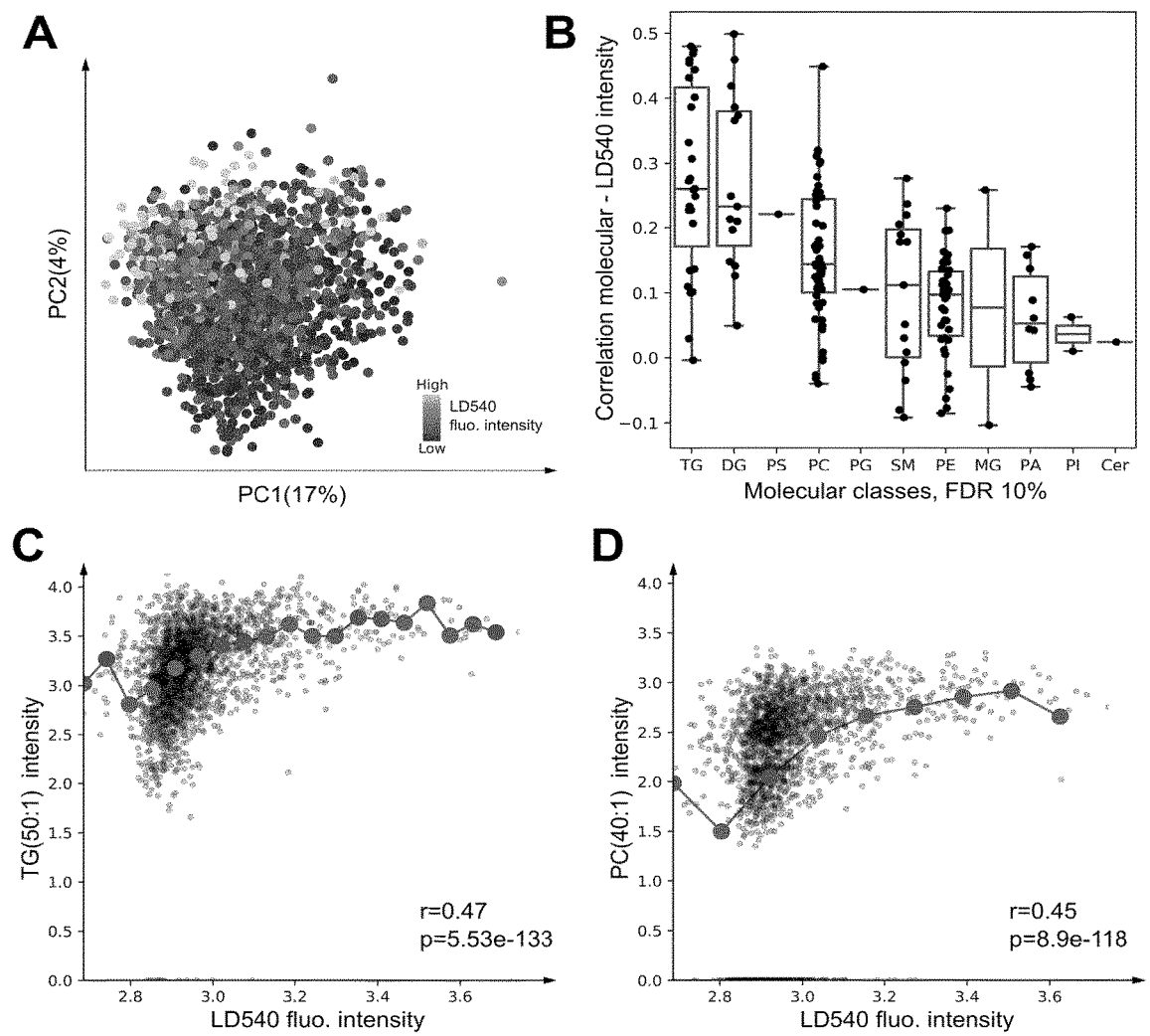

FIG. 4: Single-cell analysis of the molecular composition of lipid droplets in HepaRG hepatocytes stimulated with TNF-α. A. Single-cell PCA analysis of the single-cell metabolite profiles; one dot represents one cell, colored by log 10 of single-cell LD540 fluorescence intensity. B. Correlations between LD540 fluorescence measure and lipid intensities across n=2370 cells; one dot is one of 167 detected lipid species. C-D. Single-cell scatterplots showing relations between LD540 fluorescence and selected lipids, TG(50:1) and PC(40:1); red dots represent averages molecular intensities for regular bins of fluorescent intensity, r and p-values are for Spearman correlation between fluorescent and molecular intensities.

Figure 5:
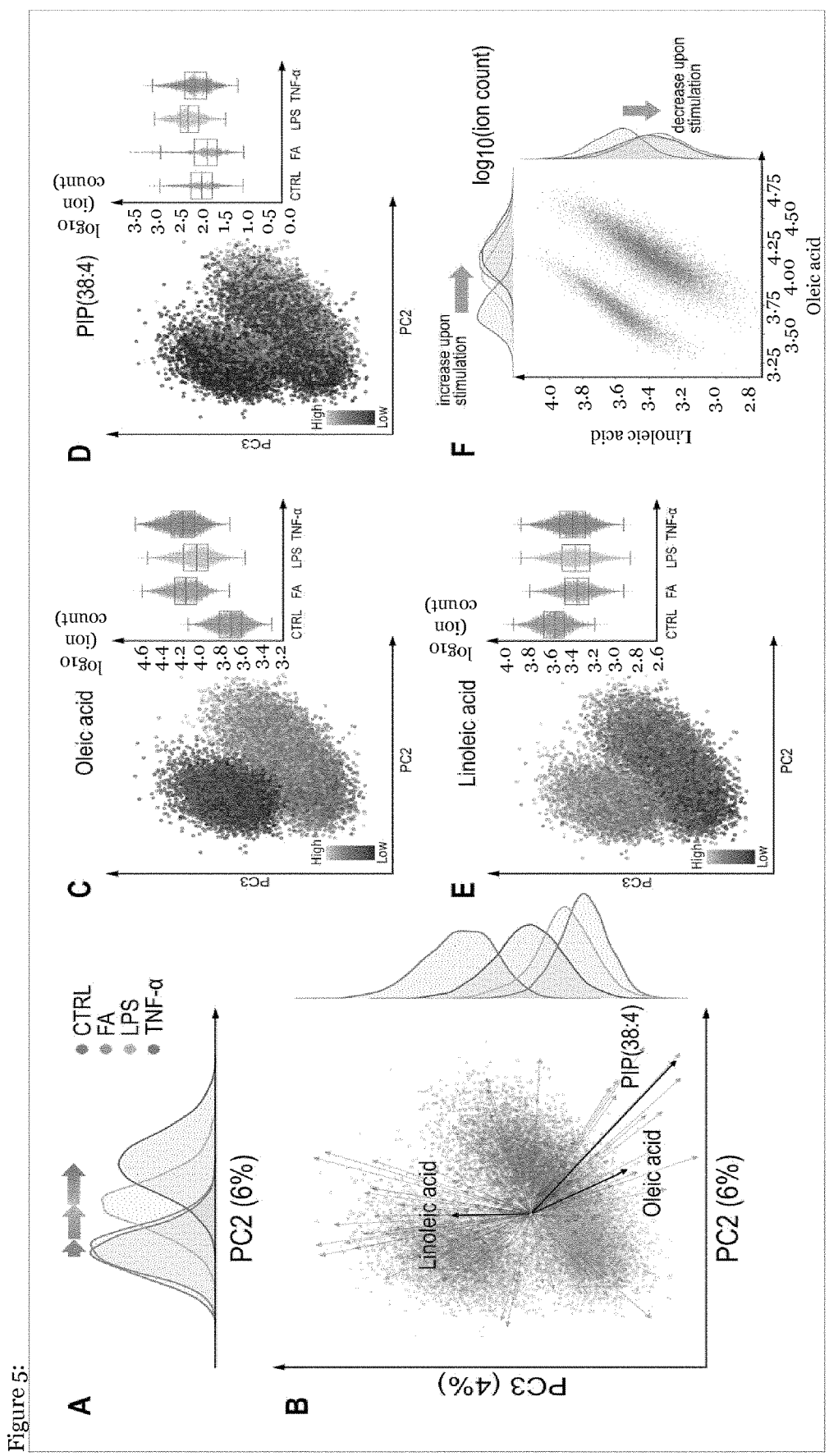

FIG. 5: Single-cell molecular trends of induced hepatocytes (n=22258). CTRL: control cells (n=5654); FA, LPS, and TNF-α: cells subjected to fatty acids (oleic acid, palmitic acid) (n=4972), the fatty acids and LPS (n=5062), the fatty acids and TNF-α (n=6570), respectively. For each cell, its metabolic profile represents normalized intensities of 134 metabolites. A: Second principal component represents molecular differences between the control and stimulated cells with the expected levels of responses (LPS stronger than FA, TNF-α stronger than LPS). B: PCA plot of the second and third principal components, one dot representing one cell, color-coded by the condition, with the biplot vectors representing contributions of the 134 individual detected metabolites to the PCA plot. Three exemplary metabolites are highlighted. C-E: Normalized single-cell intensities for three exemplary metabolites mapped onto the PCA plot and the Tukey box plots of their intensities per condition (25% and 75% percentiles shown, with whiskers at the distance of 1.5 times of the interquartile range from each quantile). Only cells with non-zero normalized ion intensity are shown. F: Single-cell scatterplot of intracellular linoleic acid vs. oleic acid in all cells, illustrating the increase of oleic acid and decrease of linoleic acid upon stimulation and a tight and condition-independent correlation of the single-cell intracellular levels of the oleic acid and linoleic acid.

Figure 6:
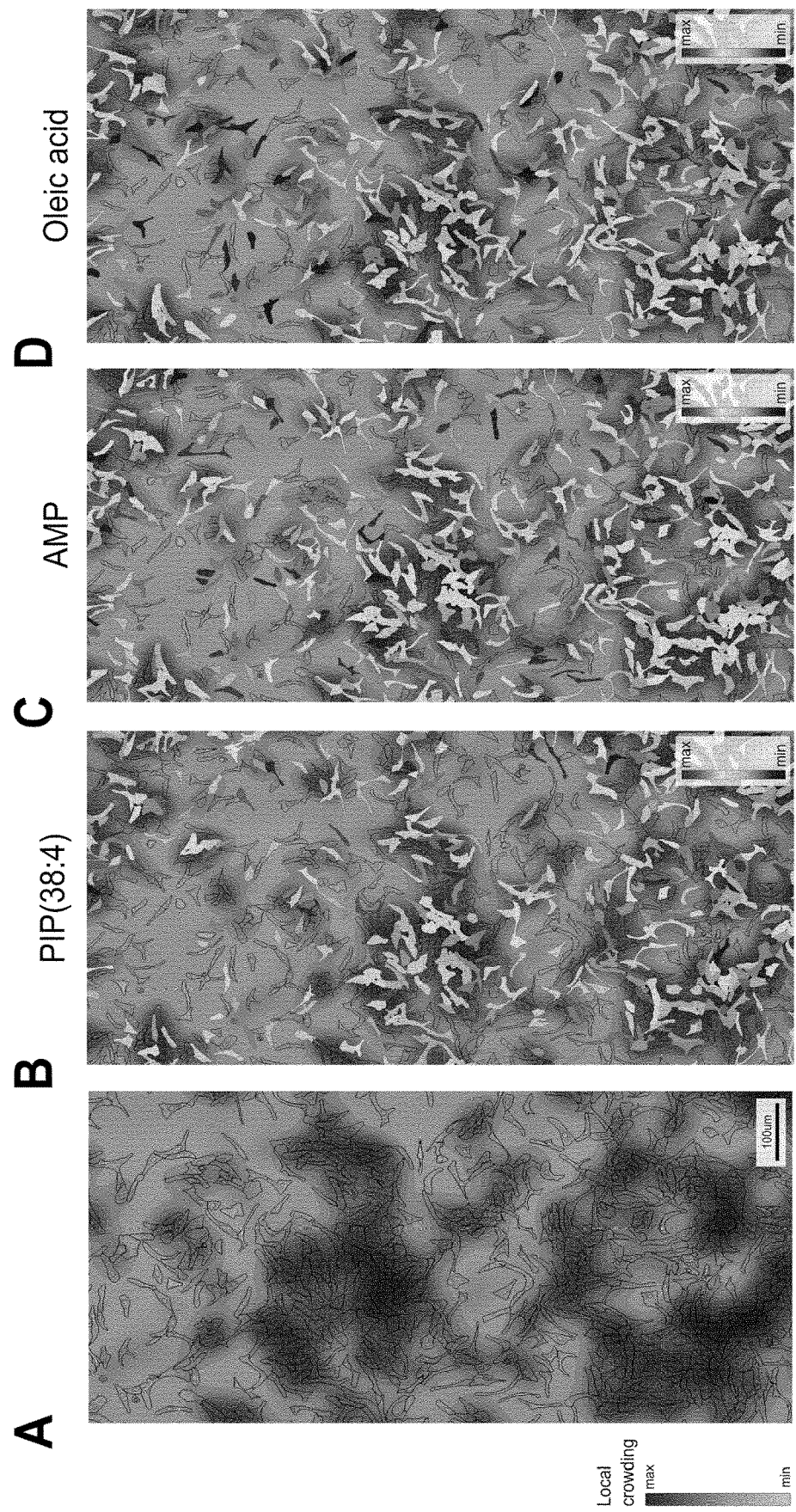

FIG. 6: Single-cell intensities of metabolites and lipids in hepatocytes. A: Overlay of the bright-field and LD540-fluorescent microscopy images of the hepatocytes (TNF-α condition) showing the cell outlines and darkened areas of high spatial crowding. B-D: Single-cell molecular images of exemplary metabolites: PIP(38:4), AMP, and oleic acid. Spearman $r_s$ (p-values) of correlation between single-cell metabolite intensities and spatial crowding are 0.36 (4e-145), −0.01 (0.67), −0.21 (6e-20) for PIP(38:4), AMP, and oleic acid, respectively. PIP(38:4) is the most correlated among all detected metabolites that might indicate its association with the cell-to-cell contact.

Figure 7:
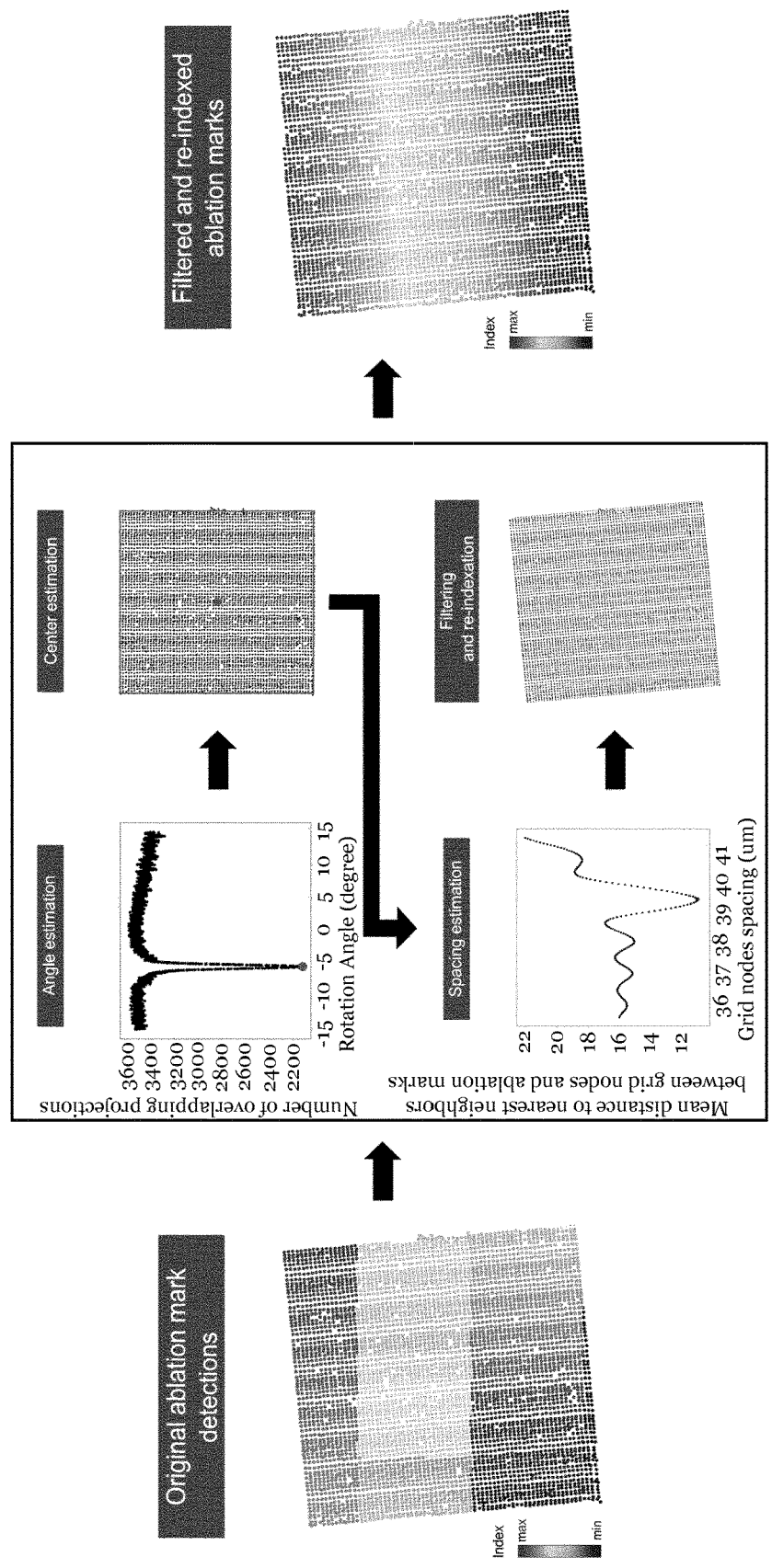

FIG. 7: Illustration of the procedure for fitting a theoretical rectangular grid to the ablation marks segmented in the post-MALDI microscopy images and re-indexing them to associate each detected ablation mark with a MALDI spectrum.

Figure 8:
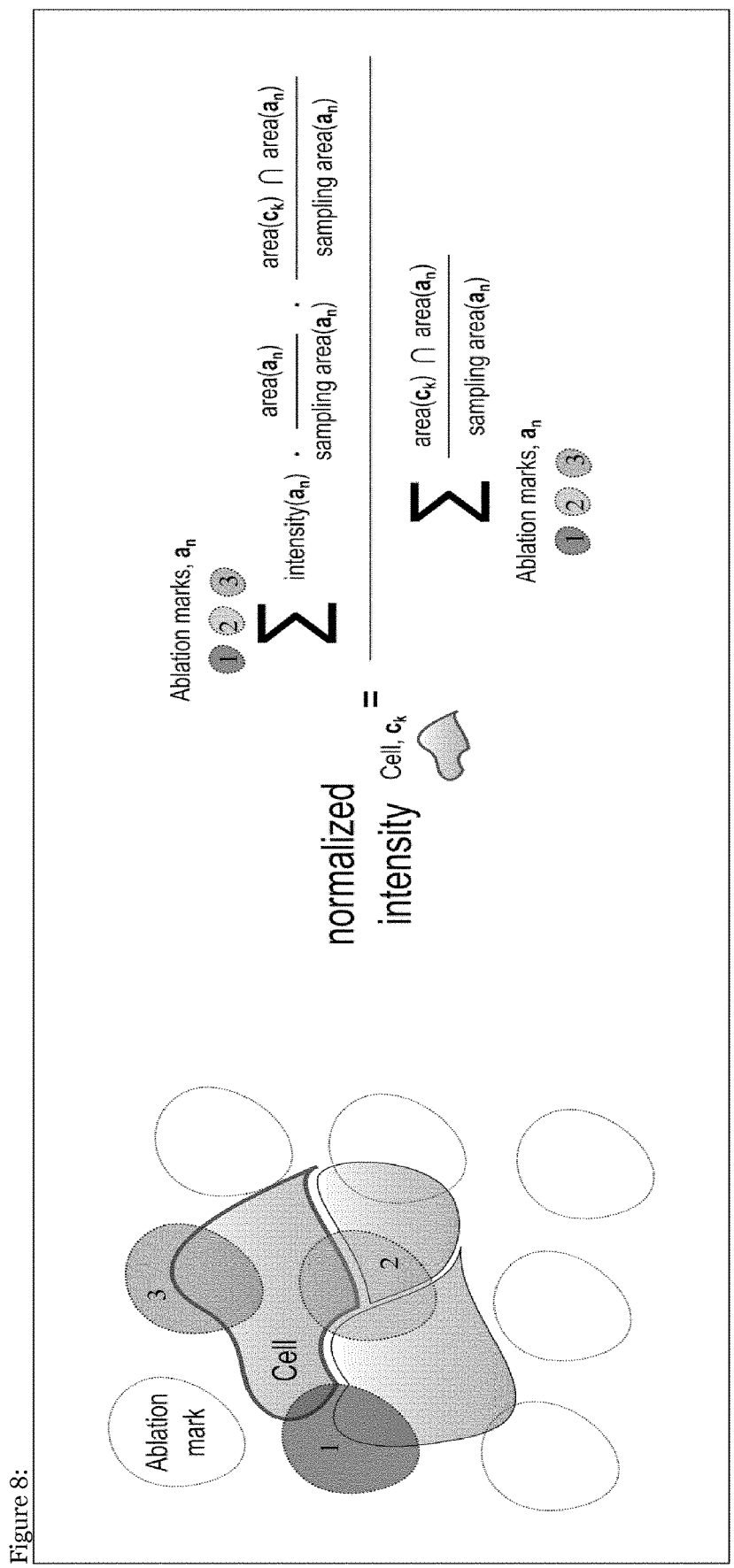

FIG. 8: Illustration of the normalization approach for estimating the molecular intensity of a cell by deconvolving mass spectrometry intensities measured at ablation marks which can only partially sample a cell or represent ions from different cells. area($a_n$) represents the area of the ablation mark; sampling area($a_n$) represents the area of the ablation mark overlapped with any cell; area($c_k$) represents the area of the cell; all areas are computed in microscopy pixels.

EXAMPLES

An object of the present invention was to provide correlative light microscopy-imaging mass spectrometry that allows the analysis of individual cells in a cell population. An example of the method of the invention is provided in the following. The overview of the main method steps is shown in FIG. 1. In brief, the inventors infected cultured HeLa cells with mCherry Salmonella enterica, subjected them to AP-SMALDI-Orbitrap imaging MS, annotated metabolites using an FDR-controlled bioinformatics approach (Palmer et al. 2017 *Nature Methods*), and overlaid them manually with fluorescence images. Another correlative light microscopy-imaging MS study on adherent cells is shown in FIG. 2.

Example 1: Detailed Description of the Method of the Invention

Step 1: Cell Culture

This step concerns the culturing of a monolayer of cells to be analyzed by the method of the invention. Cells should be cultured in monolayer on a translucent support to allow for imaging of their phenotype by microscopy to detect cell areas using bright-field microscopy and to obtain cells fluorescence readout. The inventors evaluated the workflow on several cell lines, including macrophages, HeLa cells, intestinal cells, and human hepatocytes. The cells were fixed in 4% paraformaldehyde for 5 min. The cells nuclei were stained with the Hoechst staining. After fixation, the cells were dried in a vacuum chamber until analysis.

Step 2: Microscopy

This step concerns obtaining a bright-field and fluorescence microscopy image of the cell monolayer. Pen marks using a black 140S pen (Edding, Germany) were drawn on the back side of the coverslip (opposite to where cells are grown) outlining the perimeter of the area with cells, to be used later on as fiducial markers for image registration. For both bright-field and fluorescence microscopy, a tiled acquisition was performed with the scanning microscope Nikon Ti-E with a motorized stage before and after MALDI imaging mass spectrometry. Images were stitched together using the Fiji stitching plugin from Preibisch et al. (Preibisch, Saalfeld, and Tomancak 2009). This plugin outputs a stitched image and the registered coordinates of each tile image after stitching as a text file.

Step 3: Single Cell Segmentation

For cell segmentation, the CellProfiler software (Carpenter et al. 2006) was applied to the brightfield and fluorescent microscopy images taken before MALDI imaging. The signal coming from Hoechst staining was used to find nuclei. The coordinates of the nuclei are then used as a seed for cell segmentation which was done using a watershed algorithm applied to the microscopy image. CellProfiler outputs an image in which the pixels over each cell area are assigned to the corresponding cell indices.

Step 4: MALDI Imaging Mass Spectrometry

This step concerns obtaining MALDI imaging mass spectrometry (imaging MS) data from the cell monolayer. MALDI matrix was deposited onto the cell monolayer either by sublimation using a custom-made sublimation chamber or a robotic sprayer TM Sprayer (HTX); other types of matrix application could potentially be used as well (e.g. manual sprayer). An opaque matrix coating is required in order to observe the ablation marks. MALDI imaging was then performed on the sample using an APSMALDI-Orbitrap system (source from TransMIT gGmbH, analyzer from Thermo Fisher Scientific). A total of 30 of laser shots per pixel were used. The laser focus size was estimated to be 20 micrometer. Application of the MALDI laser resulted in an ablation mark per pixel that is not of square size due to the properties of the laser. It is important that ablation marks do not overlap with each other and are visible by the bright-field microscopy. The raw imaging MS data was converted into the imzML format using the software ImageQuest (Thermo Fisher Scientific). For metabolite annotation, the imzML files (both .imzML containing metadata and .ibd containing spectra) the inventors used an FDR-controlled bioinformatics approach the inventors recently developed and implemented by us (Palmer et al. 2017 *Nature Methods*).

Step 5: Ablation Mark Segmentation

This step concerns performing image analysis of the bright-field microscopy images obtained after MALDI imaging with the aim to detect MALDI ablation marks in a procedure the inventors call ablation mark segmentation. This was performed with a custom Matlab script within a Python pipeline using the Python Matlab engine. The key idea for a high-quality segmentation of the ablation marks in a noisy bright-field image is to apply Fourier transformation. Using Fourier transformation improves segmentation as marks locations are organized in a regular periodic or nearly-periodic grid pattern. The inventors computed the two-dimensional Fast Fourier Transform (FFT) of each tile microscopy image after the MALDI imaging. Then, in the Fourier domain, the inventors extracted the component corresponding to the ablation marks as follows. The inventors applied a broad Gaussian filter to the results of two-dimensional FFT, then subtracted the results of the Gaussian filtering from the original results of two-dimensional FFT. Then, the inventors constructed a binary mask of to-be-considered 2D FT coefficients by thresholding all coefficients where the threshold is selected based on the histogram of all FT coefficients, and applying a morphological image dilation to the binary mask (considered as an image). Finally, the inventors considered only the FFT coefficients within the binary mask and computed the inverse FFT that resulted in an improved image showing ablation marks. Then, the inventors applied a contrast enhancement and background removal by means of the top-hat filtering. The image was then binarized using the Otsu threshold. Finally, the inventors applied the morphological image analysis (closing then opening) to minimize the artifacts that resulted in a binary image of the MALDI ablation marks.

The coordinates of individual ablation marks were computed by the centroid estimation on each feature from the ablation marks image.

The centroid coordinates of the ablation marks from each image are then transformed and put together using the registered images coordinates from the textfile output by the FIJI stitching algorithm. As the ablation mark detection can suffer from noise, it is sometimes required to manually select the detections from the ablation marks. The area of each ablation mark is evaluated using a custom implementation of a region growing algorithm which uses the centroids coordinates as a seed.

As the acquisition pattern of the MALDI follows a grid, a model of a grid is fitted onto the ablation mark centroid coordinates. It allows to index the ablation mark coordinates as well as correcting misdetections (double, missing and artifacts). The angle of the grid is evaluated by reporting the number non-zero bins from the histogram of the orthogonal projection of the ablation mark coordinates at different angles. The angle giving the minimum of non-zero bins is the alignment angle by respect to the projection axes. The borders of the ablation marks coordinates are estimated allowing the estimation of the center of the acquisition grid. The step between ablation marks (lattice) as well as the acquisition dimensions are both obtained from the UDP file outputted by the MALDI source control software MCP: Master control program ((C) 2005-2015 TransMIT GmbH). The acquisition dimensions, lattice, center coordinates and angle are used to generate a model of a grid to match the ablation marks coordinates. The distance between each point of the grid model and the ablation marks is evaluated using the python KDTree algorithm from scipy. The inventors then used the Python implementation of the basinhopping optimizer from scipy to find the best parameters combination of the grid model which minimizes its mean distance to the ablation marks coordinates. Once the optimization is performed, the first closest neighbor from the grid to the ablation mark coordinates is kept. That way, the ablation marks are sorted with the correct index and extra detection are removed.

Step 7: Registration of MALDI and Microscopy Images

The inventors used SURF features (Bay, Tuytelaars, and Van Gool 2006) MatLab implementation to detect features corresponding to the pen marks drawn on the back of the coverslip. The features coordinates are recorded for the microscopy dataset taken before and after MALDI acquisition. The coordinates of the features from the dataset taken after MALDI are transformed using the Python module skimage. The translation and rotation parameter combination leading to the minimal distance between the features from the dataset taken before and after MALDI are found using the basinhopping optimizer algorithm implemented in the Python module scipy. Those parameters are used to transform the ablation mark coordinates which can then mapped on the dataset taken before MALDI.

Step 6: Downstream Analysis and Visualization

The data from the metabolite annotation pipeline have very high dimensionality where each metabolite annotation corresponds to one dimension. For visualization purposes, the inventors used unsupervised dimensionality reduction techniques such as Principal Component Analysis (PCA) or t-Distributed Stochastic Neighbor Embedding (t-SNE) (Maaten and Hinton 2008). The latter was demonstrated to be efficient for visualizing single-cell transcriptomics data and revealing cells of similar transcriptomic profiles. FIG. 3 shows how subpopulations of cells determined by their molecular phenotypes can be discovered and interpreted. In the example of FIG. 3, the inventors discovered a subpopulation of cells of specific metabolite phenotype that was associated with the high-fluorescence optical phenotype.

Example 2: Analysis of Intracellular Metabolome Changes in Stimulated Hepatocytes Using the method of the invention, the inventors investigated the molecular content of the lipid droplets (LDs) in hepatocytes stimulated with several pro-inflammatory factors. Human hepatocytes exposed to inflammatory cytokines, such as TNF-$\alpha$, accumulate neutral lipids such as triglycerides and diglycerides as well as cholesteryl ester in lipid droplets, resulting in macrovesicular steatosis (U. J. Jung, M.-S. Choi, Int. J. Mol. Sci. 15, 6184-6223 (2014)). As an orthogonal measure of LD accumulation, the inventors used the fluorescent dye LD54o which stains the LD core (J. Spandl, D. J. White, J. Peychl, C. Thiele, Li, Traffic. 10, 1579-1584 (2009)). Monolayers of differentiated human hepatocytes were cultured (the HepaRG cell line) on glass microscopy coverslips and stimulated with TNF-$\alpha$ as described in the Methods. Fluorescence of the LD540 staining for individual cells from the pre-MALDI fluorescent microscopy images was quantified.

The inventors then measured their metabolites intensities for 167 metabolites annotated by METASPACE with FDR≤10%. The 2,5-dihydroxybenzoic acid (DHB) MALDI matrix was used that is preferential for neutral and polar lipids composing LDs such as tri-, di-, and mono-glycerides, phosphatidylcholines, phosphoethanolamine, and other phospholipids. Single-cell principal component analysis of the metabolic profiles of 167 metabolites from 2370 cells visualizes that single-cell lipidome detected by the method of the invention correlates the single-cell lipid measure by LD540 fluorescence (FIG. 4A) with PC1 and PC2 correlated with LD540 intensity with Spearman rs values of −0.29 and 0.29 respectively (p-values 6.44e-48 and 1.65e-47). Correlative analysis between the LD540 fluorescence and lipids intensities showed that the lipid classes of diglycerides (DGs), triglycerides (TGs), phosphatidylcholines (PCs) are the key constituents of the LDs (FIG. 4B). This corroborates existing knowledge about DGs and TGs composing the core of LDs as well as PCs composing the surface of LDs as well as the TGs accumulation being the key defining property of hepatic steatosis (C. Ress, S. Kaser, World J. Gastroenterol. 22, 1664-1673 (2016)). FIG. 4C-D show examples of relations between single-cell lipid droplet fluorescence readout (log 10 of average LD540 fluorescence per cell) and the single-cell lipid intensity for the triglyceride TG(53:3) and phosphatidylcholine PC(40:1). This illustrates that the method of the invention is able to reproduce single-cell lipid accumulation seen with the LD540 LD-specific fluorescent staining but in addition provides molecular insights about the molecular composition of LDs.

Example 3: Single-Cell Trends in Induced Hepatocytes

The inventors exploited the method of the invention to investigate changes in intracellular metabolome caused by different pro-inflammatory factors, considering the following conditions: (i) CTRL, untreated cells, (ii) FA, cells stimulated with an excess of fatty acids (oleic acid and palmitic acid) similar to the inventor's previous in vivo work where the diet enriched with these FAs recapitulated key features of human metabolic syndrome nonalcoholic steatohepatitis (NASH) and hepatocellular carcinoma (HCC) in mouse (M. J. Wolf et al., Cancer Cell. 26, 549-564 (2014)), (iii) LPS, cells stimulated with both FAs and a lipopolysaccharide, a pathogen-associated molecular pattern and (iv) TNF-α, cells stimulated with both FAs and the cytokine Tumor Necrosis Factor alpha, the central pro-inflammatory cytokine of the tumor necrosis factor superfamily (TNFSF). For each of the four conditions, three culture wells were considered as technical replicates with a randomized design to minimize the potential measurement bias by the batch correction, which provided us with 22258 cells in total.

Principal Component Analysis (PCA) of single-cell metabolite profiles shows a clear molecular separation between untreated and stimulated cells (FIG. 5). The second principal component (FIG. 5A) captured the populations of cells ordered according to expected levels of the response. Addition of either TNF-α or LPS together with FAs is expected to increase the response. Addition of the cytokine TNF-α is expected to induce a strong and specific effect downstream of TNFR signaling whereas the response of the cells to LPS is broader, activates TLR-signaling and induces inherent TNF-α secretion.

The inventors have identified contributions of individual metabolites to the molecular trends shown in FIG. 5B. As expected, supplementing oleic acid in the stimulated conditions (FA, LPS, TNF-α) causes an increase of its intracellular level. Interestingly, linoleic acid shows a decrease in the stimulated conditions compared to the CTRL cells. This inverse relation between the levels of oleic and linoleic acids was earlier observed in human plasma in physiological experiments upon sustained consumption of olive oil and was associated with the lipid oxidative damage. The single-cell scatterplot of linoleic acid vs oleic acid (FIG. 4F) shows not only this inverse relationship that could be discovered using a bulk analysis. It shows that the single-cell levels of linoleic and oleic acids are tightly correlated and, moreover, the slopes of this correlation are independent on the condition that might indicate a general co-regulation mechanism of these two fatty acids.

Example 4: Spatio-Molecular Organization of Hepatocyte on Single-Cell Level

The inventors investigated the spatio-molecular organization of hepatocytes (FIG. 6). Among all metabolites detected, correlation analysis revealed the phosphatidylinositol phosphate PIP(38:4) to be the most associated with the cell-cell contact with the Spearman rs=0.36, p-value=2.5e-57. PIP(38:4) is a precursor of PIPS, a signaling phospholipid in the plasma membrane known to have transporter functions that, in the absence of gap junctions in the considered hepatocytes, can explain how physical contact between cells can induce the locally-concerted molecular response. Not all detected metabolites were found to be positively correlated with the cell-cell contact. For example, adenosine monophosphate (AMP) showed no correlation and oleic acid showed slightly negative correlation (FIG. 6C-D).

Materials and Methods

Cell Culturing and Stimulation

HepaRG cell culture (done in kind collaboration with the lab of Matthias Heikenwälder, German Cancer Research Center) and differentiation was performed as described elsewhere. $2.2 \times 10^5$ HepaRG cells were cultured on 4-well-glass chamber slides (Lab-Tek II, CC2) (Thermo Fisher Scientific, Bremen, Germany) ($5.5 \times 10^4$ cells/well). The cells were stimulated with fatty acids: oleic acid (66 μM) and palmitic acid (33 μM), TNF-α (final conc. 50 ng/ml) (Recombinant Human TNF-alpha, and Systems) or LPS (100 ng/ml) (LPS from *E. coli*) (Sigma Aldrich, Darmstadt, Germany) in Williams E Medium (William's Medium E, with stab. Glutamine, without Phenol red, with 2.24 g/l $NaHCO_3$) (PAN Biotech) for 24 h. For each of the four conditions, cells were seeded in three different wells which were considered as technical replicates. Each After washing, cells were fixed for 15 min with 4% paraformaldehyde (Sigma Aldrich) at room temperature. Then the cells were washed and stained with Hoechst (1 μg/ml) (Hoechst 33342) (Thermo Fisher Scientific) and LD540 (0.1 μg/ml) in PBS for 30 min at room temperature. After washing, cells were stored in dH2O at 4° C. for one night maximum. The plastic walls of the labtek were removed and the cells were dried in a Lab Companion™ Cabinet Vacuum Desiccator for 16 h at room temperature and −0.08 MPa. After complete desiccation of the cells, pen marks are manually drawn on the slide using a black alcohol pen model 140s black (Edding, Ahrensburg, Germany) to keep track of the slide orientation and for image registration. The marks were drawn on the same side as the cells. Cells are kept at 4° C. upon observation. For the following experiments, the samples were analyzed by the microscopy and imaging mass spectrometry following a randomized experimental design.

Pre-MALDI Bright-Field and Fluorescence Microscopy of Cells

Fixed cells were sequentially observed the camera Nikon DS-Qi2 (Nikon Instruments) with the Nan Fluor 10× (NA 0.30) objective (Nikon Instruments) mounted on the Nikon Ti-E inverted microscope (Nikon Instruments) in bright-field and fluorescence (620 nm and 460 nm). The pixel size was 0.73 um. The microscope was controlled using the Nikon NIS Elements software. The tiled acquisition of each cell culture area was performed using the JOB functionality of the NIS software. Stitching of tiled frames was performed using the FIJI stitching plugin.

MALDI Imaging Mass Spectrometry

Humidity and temperature levels in the mass spectrometry room were monitored and controlled during the whole experiment and were within 44-63% and 21.1-23.7° C. The matrix 1,5-diaminonaphtalene (DAN) (Sigma Aldrich) 10 mg/ml dissolved in 70% acetonitrile was applied onto the dried cells on the labtek slides by using a TM-Sprayer robotic sprayer (HTX Technologies, Carrboro, N.C., USA). Spraying parameters were as following: temperature=90° C., number of passes=8, flow rate=0.07 ml/min, velocity=1350 mm/min, track spacing=3 mm/min, pattern=CC, pressure=10 psi, gas flow rate=2 l/min, drying time=15 sec, nozzle height=41 mm. The estimated matrix density was of 0.001383 mg/mm2. For MALDI imaging mass spectrometry, the glass slides with the dried cells on them were mounted onto a custom slide adaptor and loaded into the AP-SMALDI source (Transmit, Giessen, Germany). The x-y raster was set to 50 um, the focus was maximized manually using the source cameras with the focused beam size estimated to be between 15 and 30 µm. For each pixel, the spectrum was accumulated from 30 laser shots at 1,000 Hz. Negative mode MS analysis was performed in the full scan mode in the mass range of 200-1100 m/z (resolving power R=140,000 at m/z=200) using an QExactive Nus mass spectrometer (ThermoFisher Scientific). MS parameters in the Tune software (version 2.5 Build 2042, ThermoFisher Scientific) were set to the spray voltage of 4.10 kV, S-Lens 80 eV, capillary temperature 250 C. The data was converted from the RAW format into the imzML format containing only centroided data using the ImageQuest software, v.1.1.0 (ThermoFisher Scientific). Metabolite annotation was performed using the METASPACE online platform, http://metaspace2020.eu with the bioinformatics for False Discovery Rate-controlled annotation published by us earlier with the m/z tolerance of 3 ppm and FDR of 10%, 20%, and 50% against the HMDB metabolite database v2.5.

Post-MALDI Microscopy to Detect MALDI Ablation Marks

The cells were imaged in bright-field microscopy after MALDI-imaging using the same microscopy setup and parameters as described earlier in the pre-MALDI microscopy section to define the positions of the ablation marks with respect to the fiducial marks.

Association of Laser Ablation Marks With Single Cells

This is the key part of the method as it solves the challenge that single cells are not visible in the post-MALDI microscopy images due to the opaque layer of MALDI matrix covering cells. Here, ablation marks left by the MALDI laser were associated with single cells in three steps: i) cells segmentation in the pre-MALDI microscopy images, b) detection of laser ablation marks in post-MALDI microscopy images, c) matching between ablation marks and MALDI mass spectra and d) co-registration of pre- and post-MALDI microscopy images to overlay the ablation marks with the segmented single cells.

In step a), cells were segmented using a custom pipeline in the CellProfiler software where the DAPI staining channel was used to generate seeds for a region growing algorithm detecting cells boundaries in the LD540-staining channel.

In step b), the inventors first denoised the bright-field microscopy images by applying a low-pass filter in the 2D Fourier frequency domain, in particular to exploit both the regular distances between ablation marks as well as the repeated shape of the ablation mark itself. Then, the inventors applied a contrast enhancing filter (using the imadjust function in Matlab) and Otsu's thresholding method to binarize the image (using the imbinarize function in Matlab). Then, the inventors applied morphological image analysis operations of closing and then opening to fill in the holes in the image and remove individual noisy pixels (using the imclose and imopen functions in Matlab). This resulted in estimations of the centre of mass of each ablation mark.

In step c), the inventors fitted a theoretical rectangular grid to the ablation marks. The numbers of X- and Y-grid steps were defined as set up during the MALDI acquisition. The center of the acquisition region was considered as the center of the grid. The orientation of the grid with respect to the post-MALDI microscopy image was optimized by finding an angle which resulted in best overlap between the grid lines and the detected ablation marks. The X- and Y-spacing of the grid were optimized by minimizing the distance between the grid nodes and the center of mass of the nearest neighbor ablation mark. Then, only ablation marks which were the nearest neighbors to the grid nodes were taken and re-indexed (FIG. 7). This provided X- and Y-coordinates for each ablation mark associated with a collected MALDI spectrum. In order to obtain more correct estimations of the ablations marks areas used later for normalization, their segmentation was further improved by applying a region-growing algorithm by using the open-source implementation by Daniel Kellner available from the MatlabExchange (https://de.mathworks.com/matlabcentral/fileexchange/32532-region-growing--2d-3d-grayscale).

In step d), co-registration of pre- and post-MALDI microscopy images was done based on the pen marks drawn on the edge of the wells used as fiducials. The inventors first segmented the pen marks in both pre- and post-MALDI bright-field microscopy images using Otsu's intensity thresholding method. Then, the inventors used the basin-hopping optimization algorithm (Python implementation from the scipy package vo.18.1) to find the best linear transformation matching the coordinates of the edges of the pen marks between the pre- and post-MALDI images. The optimal linear transformation was applied to the post-MALDI microscopy images to map the ablation marks to the pre-MALDI microscopy images.

Single-Cell Intensity Normalization

A normalized intensity of each metabolite in a single cell was constructed as follows (see FIG. 9). For each cell, the inventors considered all ablation marks overlapping with the cell area and selected the associated ablation marks which overlap with the cell by over than 30% of their ablation area. The metabolite intensities coming from an ablation mark were normalized by dividing them by the ratio of the sampling area (defined as the number of pixels of the intersection of the ablation mark and any cell region) to the area of the ablation mark. Finally, for each cell its normalized metabolite intensities were calculated as the weighted average normalized intensities of the associated ablation marks where the weights are defined as the ratio of the shared pixels. In order to account for the variations in permeabilization efficiency between the biological replicates, single-cell LD540 fluorescence intensities were normalized by dividing them by the median DAPI intensity (median over a well).

Selecting Intracellular Metabolites

The inventors selected metabolite annotations corresponding to intracellular metabolites as follows. First, for each ablation mark the inventors assigned to it the inside-cells label having values either of zero or one based on whether the mark has any overlap with any cell. Then, for each metabolite ion image, its intensities were binarized to zero-ones values by selecting a threshold leading to the highest Pearson correlation with the inside-cells labels. The threshold value was found using the basin-hopping optimization algorithm. In order to consider only intracellular metabolites for further analysis, the inventors selected those metabolite annotations whose binarized ion images were correlated with the inside-cells labels with the Pearson correlation higher than 0.25. Among them, the inventors considered the metabolite annotations which were shared by at least 3 samples (out of 12 overall) that led to 134 annotations. For each of these metabolites annotations, the inventors pulled the ion images with the m/z tolerance of 3 ppm from the imzML files.

Cell Filtering and Batch Correction

The inventors filtered out 5% of cells (1240 cells out of 23498 overall) with the lowest metabolite yield, namely the cells which had most zero-valued metabolites annotations, following the approach well-accepted in single-cell transcriptomics. To compensate for the batch effect between the biological replicates within each condition, the inventors applied the combat batch correction algorithm originally developed for single-cell transcriptomics data using its open-source Python implementation neuroCombat available at https://github.com/ncullen93/neuroCombat.

Data Visualization

All plots were generated in Python, version 3.6.2, by using the packages matplotlib 2.1 and seaborn 0.8.1. The Python package scikit-learn 0.19.1 was used for the Principal Component Analysis.

REFERENCES

Caprioli R M, Farmer T B, Gile J. 1997. "Molecular imaging of biological samples: localization of peptides and proteins using MALDI-TOF MS". Analytical Chemistry, 69: 4751-4760

Bay, Herbert, Tinne Tuytelaars, and Luc Van Gool. 2006. "SURF: Speeded Up Robust Features." In Computer Vision—ECCV 2006, 404-17. Springer, Berlin, Heidelberg.

Carpenter, Anne E., Thouis R. Jones, Michael R. Lamprecht, Colin Clarke, In Han Kang, Ola Friman, David A. Guertin, et al. 2006. "CellProfiler: Image Analysis Software for Identifying and Quantifying Cell Phenotypes." Genome Biology 7 (10): R100.

Maaten, Laurens van der, and Geoffrey Hinton. 2008. "Visualizing Data Using T-SNE." Journal of Machine Learning Research: JMLR 9 (November): 2579-2605.

Palmer A, Phapale P, Chernyaysky I, Lavigne R, Fay D, Tarasov A, Kovalev V, Fuchser J, Nikolenko S, Pineau C, Becker M, Alexandrov T. 2016. "FDR-controlled metabolite annotation for high-resolution imaging mass spectrometry". Nature Methods, 14: 57-60

Preibisch, Stephan, Stephan Saalfeld, and Pavel Tomancak. 2009. "Globally Optimal Stitching of Tiled 3D Microscopic Image Acquisitions." Bioinformatics 25 (11): 1463-65.

The invention claimed is:

1. A method of single cell(s) mass spectrometry (MS) imaging, the method comprising the steps of
   (a) Culturing cell(s) on a substrate,
   (b) phenotyping the cell(s) by microscopy to obtain at least one optical image showing an optical phenotype of the cell(s),
   (c) phenotyping of the cell(s) by imaging MS to obtain an MS molecular image showing a molecular phenotype of the cell(s),
   (d) Comparing the optical image and the MS molecular image to at least one of: compare, correlate, and assign, the optical phenotype of at least one single cell with the corresponding molecular phenotype of at least one single cell,
wherein steps (b) and (c) are performed in any order/sequence.

2. The method according to claim 1, wherein the cell(s) are cultured in a monolayer of adherent cells.

3. The method according to claim 1, wherein in step (d) the MS molecular image and the optical image are correlated by direct comparison of the images.

4. The method according to claim 3, wherein the MS molecular image and the optical image are correlated by overlaying both.

5. The method according to claim 1, wherein the substrate is a translucent substrate.

6. The method according to claim 5, wherein the translucent substrate is a translucent plastic substrate or glass substrate.

7. The method according to claim 5, wherein the translucent substrate is a glass slide.

8. The method according to claim 1, wherein the microscopy is at least one of bright-field microscopy and fluorescent microscopy.

9. The method according to claim 1, wherein step (d) comprises assigning location coordinates to each cell in the MS molecular image and the optical image, and thereby assigning the optical phenotype of each cell with its molecular phenotype.

10. The method according to claim 1, wherein multiple but different optical images are obtained, and step (d) comprises comparing each of the multiple optical images to the MS molecular image to correlate/assign each optical phenotype of the multiple optical images of each cell with its molecular phenotype.

11. The method according to claim 1, wherein at least one optical image is an image of a Hoechst or other fluorescent staining of the cell(s).

12. The method according to claim 1, wherein the substrate comprises fiducial marks for image registration.

13. The method according to claim 1, wherein step (d) comprises the identification of each cell in the optical image.

14. The method according to claim 13, wherein the identification of each cell in the optical image comprises a cell segregation algorithm.

15. The method according to claim 14, wherein the cell segregation algorithm uses a Hoechst staining image to identify cell nuclei.

16. The method according to claim 1, comprising a step (c') subsequent to step (c), comprising obtaining an optical ablation mark image.

17. The method according to claim 1, wherein step (c) comprises deposition of an MS matrix to the cell(s) and subsequently performing MALDI imaging.

18. The method according to claim 17, wherein the MS matrix is an opaque MS matrix.

19. The method according to claim 1, wherein imaging MS is MALDI imaging.

20. The method according to claim 1, wherein step (b) is performed before step (c).

\* \* \* \* \*